(12) United States Patent
Hanafialamdari

(10) Patent No.: US 11,413,414 B2
(45) Date of Patent: Aug. 16, 2022

(54) METHOD AND APPARATUS FOR BREATHING ASSISTANCE

(71) Applicant: NovaResp Technologies Inc., Halifax (CA)

(72) Inventor: Hamed Hanafialamdari, Halifax (CA)

(73) Assignee: NovaResp Technologies Inc., Halifax (CA)

(*) Notice: Subject to any disclaimer, the term of this patent is extended or adjusted under 35 U.S.C. 154(b) by 711 days.

(21) Appl. No.: 16/342,724

(22) PCT Filed: Oct. 20, 2017

(86) PCT No.: PCT/CA2017/051258
§ 371 (c)(1),
(2) Date: Apr. 17, 2019

(87) PCT Pub. No.: WO2018/072036
PCT Pub. Date: Apr. 26, 2018

(65) Prior Publication Data
US 2020/0046923 A1    Feb. 13, 2020

Related U.S. Application Data

(60) Provisional application No. 62/411,251, filed on Oct. 21, 2016.

(51) Int. Cl.
*A61M 16/00* (2006.01)
*G16H 20/40* (2018.01)
(Continued)

(52) U.S. Cl.
CPC .......... *A61M 16/024* (2017.08); *A61B 5/085* (2013.01); *A61B 5/087* (2013.01); *A61B 5/091* (2013.01);
(Continued)

(58) Field of Classification Search
CPC ............ A61M 16/024; A61M 16/0003; A61M 2016/0027; A61M 2016/003;
(Continued)

(56) References Cited

U.S. PATENT DOCUMENTS 6,257,234 B1    7/2001  Sun
6,889,691 B2    5/2005  Eklund et al.
(Continued)

FOREIGN PATENT DOCUMENTS

CA    3040975 A1    4/2018
EP    1844743 A2   10/2007
(Continued)

OTHER PUBLICATIONS

International Search Report and Written Opinion dated Jan. 4, 2018 in International Patent Application No. PCT/CA2017/051258 (11 pages).

(Continued)

*Primary Examiner* — Steven O Douglas
(74) *Attorney, Agent, or Firm* — Bereskin & Parr LLP/S.E.N.C.R.L., s.r.l.; Tony Orsi

(57) ABSTRACT

Various embodiments are described herein for devices, methods and systems for a breathing assistance device controller for controlling the operation of a breathing assistance device that provides breathing assistance to a user. The controller may include sensors for measuring airflow parameters of the airflow and generating measured signals; and a processor that is electronically coupled to the sensors to receive the measured signals and to generate a control signal based on the measured signals and at least one characteristic of the user's respiratory system to adjust the operation of the breathing assistance device during use.

27 Claims, 5 Drawing Sheets

(51) Int. Cl.
  *A61B 5/085*   (2006.01)
  *A61B 5/087*   (2006.01)
  *A61B 5/091*   (2006.01)
  *A61B 5/097*   (2006.01)
  *A61B 5/00*    (2006.01)

(52) U.S. Cl.
  CPC ............ *A61B 5/097* (2013.01); *A61B 5/4836* (2013.01); *A61M 16/0003* (2014.02); *G16H 20/40* (2018.01); *A61M 2016/003* (2013.01); *A61M 2016/0027* (2013.01); *A61M 2202/0208* (2013.01); *A61M 2202/0266* (2013.01); *A61M 2230/40* (2013.01); *A61M 2230/46* (2013.01)

(58) Field of Classification Search
  CPC .. A61M 2202/0208; A61M 2202/0266; A61M 2230/40; A61M 2230/46; G16H 5/085; A61B 5/085; A61B 5/087; A61B 5/091; A61B 5/097; A61B 5/4836
  See application file for complete search history.

(56) References Cited

U.S. PATENT DOCUMENTS

| | | | |
|---|---|---|---|
| 8,973,578 | B2 | 3/2015 | Dellaca'et al. |
| 9,358,417 | B2 | 6/2016 | Meyer et al. |
| 9,668,673 | B2 | 6/2017 | Gobbi et al. |
| 11,077,282 | B2* | 8/2021 | Kwok .................. A61M 16/024 |
| 11,229,765 | B2* | 1/2022 | Bayer .................. A61M 16/0816 |
| 2008/0072896 | A1 | 3/2008 | Setzer et al. |
| 2014/0283834 | A1* | 9/2014 | Ahmad ............. A61M 16/0069 128/204.23 |
| 2015/0119743 | A1 | 4/2015 | Maksym et al. |
| 2016/0106341 | A1 | 4/2016 | Adam et al. |
| 2018/0117270 | A1* | 5/2018 | Bassin .................. A61M 16/16 |
| 2019/0217030 | A1* | 7/2019 | Burgess ............... A61B 5/0816 |

FOREIGN PATENT DOCUMENTS

| | | |
|---|---|---|
| WO | 2000/010634 A1 | 3/2000 |
| WO | 2011/006199 A1 | 1/2011 |
| WO | 2013/067580 A1 | 5/2013 |
| WO | 2015/127377 A1 | 8/2015 |
| WO | 2015/138474 A1 | 9/2015 |
| WO | 2017/136639 A1 | 8/2017 |
| WO | 2018/072036 A1 | 4/2018 |

OTHER PUBLICATIONS

Mochizuki et al., "Forced Oscillation Technique and Childhood Asthma", Allergology International, Sep. 2012, 61(3): 373-383.

Dellacà et al., "Detection of expiratory flow limitation in COPD using the forced oscillation technique", Eur. Respir. J., Feb. 2004, 23(2): 232-240.

International Search Report and Written Opinion dated May 11, 2021 in International Patent Application No. PCT/CA2021/050257 (8 pages).

Czövek et al., "Tidal changes in respiratory resistance are sensitive indicators of airway obstruction in children", Thorax, 2016, 71(10): 907-915.

* cited by examiner

METHOD AND APPARATUS FOR BREATHING ASSISTANCE

CROSS-REFERENCE TO RELATED APPLICATION

This application is a 35 USC § 371 national stage entry of International Patent Application No. PCT/CA2017/051258, filed Oct. 20, 2017, which claims the benefit of U.S. Provisional Patent Application No. 62/411,251, filed Oct. 21, 2016, entitled "METHOD AND APPARATUS FOR BREATHING ASSISTANCE"; the entire contents of each of which are hereby incorporated herein in their entirety by reference.

FIELD

Various embodiments are described herein for an apparatus and method that may be used to operate a breathing device to provide breathing assistance to a user of the breathing device.

BACKGROUND

Individuals suffering acute or chronic respiratory (COPD, asthma, ARDS) or respiratory-related conditions (e.g. sleep apnea) may require assistive devices to maintain respiratory functions at normal levels. Assistive devices such as mechanical ventilators, Positive Airway Pressure (PAP) devices or Continuous Positive Airway Pressure (CPAP) devices are common to provide breathing assistance. However, while such assistive devices are critical with respect to maintaining normal respiratory functions, these devices may also cause harm and distress to a user as a result of the stress or strain due to the amount of pressure or flow imparted on the user's respiratory system. As such, there is a desire for methods and systems to identify and minimize user harm.

SUMMARY OF VARIOUS EMBODIMENTS

In a broad aspect, at least one embodiment described herein provides a system for providing breathing assistance to a user, wherein the system comprises: a breathing assistance device that generates an airflow comprising at least one pressure impulse or a continuous pressure flow rate; an entry element that is coupled to the breathing assistance device and is worn by the user to provide the airflow to the user during use; and a breathing assistance device controller that is coupled to the breathing assistance device to adjust the operation of the breathing assistance device during use via a control signal that is generated based on airflow parameters reflecting the user's respiratory system.

In at least one embodiment, the breathing assistance device may be one of a mechanical ventilator and a continuous positive airway pressure device.

In at least one embodiment, the breathing assistance device controller comprises sensors for measuring air pressure and flow rate of the airflow and generating measured pressure and flow rate signals; and a processor that is electronically coupled to the sensors to receive the measured signals, to determine at least one respiratory system characteristic for the user based on the measured signals; to determine a comfort level index for the user that is related to their respiratory health status and is based on the measured flow rate signal and the at least one respiratory system characteristic; and to generate the control signal based on a relationship between the comfort level index and the type of breathing assistance device.

In at least one embodiment, the system comprises an actuator that is electrically coupled to and controlled by the processor to generate an airway pressure perturbation that is superimposed on the airflow that is provided to the user.

In at least one embodiment, the breathing assistance device comprises the actuator or the breathing assistance device controller comprises the actuator.

In at least one embodiment, the airway pressure perturbation is generated to have at least one frequency.

In at least one embodiment, the at least one frequency is in the range of 0.001 Hz to 100 MHz.

In at least one embodiment, the processor is configured to determine a complex respiratory impedance and a respiratory volume for the user's respiratory system based on the at least one of the measured air pressure and flow rate signals.

In at least one embodiment, the respiratory device controller is further configured to determine a phase difference between the imaginary portion of the complex respiratory impedance and the respiratory volume.

In at least one embodiment, at least one of the phase difference, the at least one frequency, a user breathing frequency, an assistance frequency of the breathing assistance device, the flow rate signal and the pressure signal is used to determine the comfort level index for the user.

In at least one embodiment, the measured signals are preprocessed before being processed by the processor, the preprocessing comprising amplification and filtering.

In at least one embodiment, the respiratory device controller has a housing with a first end that is releasably coupled to the breathing assistance device via a first airflow pathway and a second end that is releasably coupled to the entry element by a second airflow pathway.

In at least one embodiment, gaseous medication comprising one or more of steroids, oxygen, and Nitrogen is added to the air flow before providing the airflow to the user.

In another broad aspect, at least one embodiment described herein provides a breathing assistance device controller for controlling the operation of a breathing assistance device that provides breathing assistance to a user, wherein the controller comprises sensors for measuring airflow parameters of the airflow and generating measured signals; and a processor that is electronically coupled to the sensors to receive the measured signals and to generate a control signal based on the measured signals and at least one characteristic of the user's respiratory system to adjust the operation of the breathing assistance device during use.

In at least one embodiment, the controller further comprises a first airflow pathway for receiving an airflow generated by the breathing assistance device; and a second airflow pathway for providing the airflow to an entry element used by the user.

In at least one embodiment, the processor is configured to generate the control signal such that the resultant airflow generated by the breathing assistance device based on the control signal is used for the treatment of a respiratory condition.

In another broad aspect, at least one embodiment described herein provides a method of for adjusting an airflow provided by a breathing assistance device to a user, wherein the method comprises measuring airflow parameters of the airflow and generating measured signals; operating a processor that is electronically coupled to the sensors to receive the measured signals and to generate a control signal based on the measured signals and at least one characteristic of the user's respiratory system; and sending the control signal to the breathing assistance device to adjust the operation of the breathing assistance device during use.

In at least one embodiment, the act of measuring comprises measure a pressure and a flow rate of the airflow that is provided to the user and generating measured pressure and flow rate signals.

In at least one embodiment, the method further comprises determining at least one respiratory system characteristic for the user based on the measured signals; determining a comfort level index for the user that is related to their respiratory health status and is based on the measured signals and the at least one respiratory system characteristic; and generating the control signal based on a relationship between the comfort level index and the type of breathing assistance device.

In at least one embodiment, the method generally comprises using an actuator to generate an airway pressure perturbation that is superimposed on the airflow that is provided to the user while the sensors perform the measurements.

In at least one embodiment, the method further comprises determining a complex respiratory impedance and a respiratory volume for the user's respiratory system based on the measured signals.

In at least one embodiment, determining the complex respiratory impedance comprises transforming a time-domain representation of at least one of the pressure and flow rate signals into a frequency domain representation.

In at least one embodiment, the method further comprises determining a phase difference between an imaginary portion of the complex respiratory impedance and the respiratory volume.

In at least one embodiment, at least one of the phase difference, the at least one frequency, a user breathing frequency, an assistance frequency of the breathing assistance device, the flow rate signal and the pressure signal is used to determine the comfort level index for the user.

In at least one embodiment, the comfort level index may be determined at a predefined frequency that corresponds to the at least one oscillation frequency.

In at least one embodiment, the comfort level index is determined continuously or periodically.

In at least one embodiment, the method further comprises adding gaseous medication comprising one or more of steroids, oxygen, and Nitrogen to the air flow before providing the airflow to the user.

Other features and advantages of the present application will become apparent from the following detailed description taken together with the accompanying drawings. It should be understood, however, that the detailed description and the specific examples, while indicating preferred embodiments of the application, are given by way of illustration only, since various changes and modifications within the spirit and scope of the application will become apparent to those skilled in the art from this detailed description.

BRIEF DESCRIPTION OF THE DRAWINGS

For a better understanding of the various embodiments described herein, and to show more clearly how these various embodiments may be carried into effect, reference will be made, by way of example, to the accompanying drawings which show at least one example embodiment, and which are now described. The drawings are not intended to limit the scope of the teachings described herein.

Figure 1:
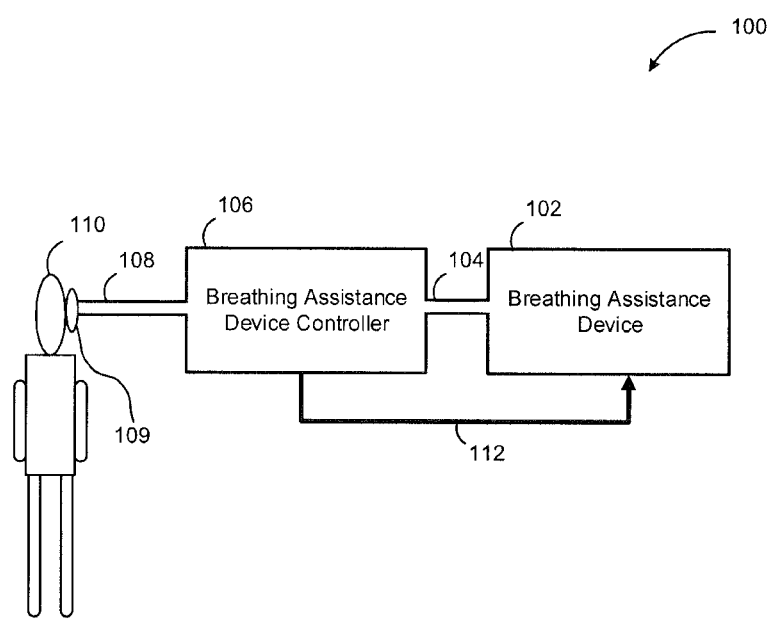
FIG. 1 is a block diagram of an example embodiment of a breathing assistance system for controlling or tuning a breathing assistance device during use by a user.

Further aspects and features of the example embodiments described herein will appear from the following description taken together with the accompanying drawings.

DETAILED DESCRIPTION OF THE EMBODIMENTS

Various embodiments in accordance with the teachings herein will be described below to provide an example of at least one embodiment of the claimed subject matter. No embodiment described herein limits any claimed subject matter. The claimed subject matter is not limited to devices or methods having all of the features of any one of the devices or methods described below or to features common to multiple or all of the devices and or methods described herein. It is possible that there may be a device or method described herein that is not an embodiment of any claimed subject matter. Any subject matter that is described herein that is not claimed in this document may be the subject matter of another protective instrument, for example, a continuing patent application, and the applicants, inventors or owners do not intend to abandon, disclaim or dedicate to the public any such subject matter by its disclosure in this document.

It will be appreciated that for simplicity and clarity of illustration, where considered appropriate, reference numerals may be repeated among the figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the embodiments described herein.

It should also be noted that the terms "coupled" or "coupling" as used herein can have several different meanings depending in the context in which these terms are used. For example, the terms coupled or coupling can have a mechanical, or a magnetic connotation. For example, as used herein, the terms coupled or coupling can indicate that two elements or devices can be directly connected to one another or connected to one another through one or more intermediate elements or devices via an electric signal, or a mechanical element, such as, conduits, for example, depending on the particular context.

It should also be noted that, as used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

It should be noted that terms of degree such as "substantially", "about" and "approximately" as used herein mean a reasonable amount of deviation of the modified term such that the end result is not significantly changed. These terms of degree may also be construed as including a deviation of the modified term such as, but not limited to, 1%, 2%, 5% or 10%, if this deviation would not negate the meaning of the term it modifies.

Furthermore, the recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about" which means a variation of up to a certain amount of the number to which reference is being made if the end result is not significantly changed, such as, but not limited to, 1%, 2%, 5% or 10%, for example.

Oscillometry, also known as the forced oscillation technique (FOT), may be performed within the field of respiratory diagnostics by superimposing fluctuations on airway pressure while a user is breathing normally and measuring the resultant pressure and flow rate to determine the mechanical properties of the user's respiratory system. For example, the measured pressure and flow rate may then be used to determine the mechanical impedance of the respiratory system. This mechanical impedance is the ratio of the oscillatory pressure to the flow rate in the frequency domain, which can be expressed as a complex quantity as a function frequency. More specifically, the real part of the mechanical impedance may be regarded as the respiratory system resistance ($R_{rs}$) and the imaginary part can be regarded as the respiratory system reactance ($X_{rs}$).

When the complex mechanical impedance of the respiratory system is described, it is generally common to present the average $R_{rs}$ and average $X_{rs}$ behavior over a frequency range of interest. These average values can normally be computed from averaging impedance values estimated using frequency domain methods such as by performing Fourier transforms on the measured pressure and flow values taken from multiple finite overlapping time windows, or from averaging over a time course computed from recursive time domain methods that can also effectively examine short duration overlapping time periods.

However, the temporal variations that occur in $R_{rs}$ and even in $X_{rs}$ during respiration may contain information related to the user's breathing and their respiratory system. This variation can be determined using a frequency domain technique such as the short-time-Fourier transform (STFT) or the Wavelet transform. Although it has been established that variations in the amplitude of $X_{rs}$ between inspiration and expiration contains signs of respiratory health, the inventor has determined that variations in the phase of $X_{rs}$, specifically the differences between the phase of determined $X_{rs}$ and volume at the oscillation frequency such as 5 Hz, which may be used for FOT, can be used to determine the overall health of an individual's respiratory system or identify potential respiratory conditions. This has not been determined by others in this field.

The reactance $X_{rs}$ can also be considered to be the portion of the measured pressure signal that is in phase with measured volume signal (Hiroyuki Mochizuki et al., "Forced Oscillation Technique and Childhood Asthma", Allergology International, Volume 61, Issue 3, 2012, pages 373-383). However, the phase difference between airflow and reactance $X_{rs}$ can be the source of the resistance amplitude and frequency dependence of resistance $R_{rs}$, and the inventor has determined that a proportion of this phase difference can be used to establish a comfort level index that is based on a health status of the user and can therefore be used to identify the level of distress being experienced by a user. Conventionally, this has never been done and advantageously this may be used to improve the respiratory health status of the user in a short period of time. This observation was made by the inventor when analyzing data obtained from people with respiratory disease, such as in, for example, Chronic Obstructive Pulmonary Disease (COPD) where people suffer from Expiratory Flow Limitation (EFL). For example, this may be seen by reviewing data shown in FIGS. 1 and 3 in R. L. Dellaca et al. ("Detection of expiratory flow limitation in COPD using the forced oscillation technique", Eur. Respir. J. 2004; 23: 232-240) where the inventor realized that within-breath reactance is in fact not completely in phase with volume which shows that phase difference is related to disease/status of respiratory health. This has not been noticed or used by other researchers or engineers in this field.

In a similar fashion, the distress that may be experienced by a user who is using a breathing assistance device may be determined by determining the comfort level index. Depending on the comfort level index, which is a number, the operating parameters of the breathing assistance device may then be adjusted to ensure that the user of the breathing assistance device experiences minimal distress. Accordingly, the comfort level index can be used to generate a feedback control signal that is used to control the operation of the breathing assistance device. The comfort level index may be determined for a given time period during which many numbers are generated which can be collectively referred to as a comfort level index signal. The comfort level index signal can be used to control the breathing assistance device over the given time period.

Previously it was not possible to determine the respiratory distress of the user of a breathing assistance device in an automated fashion. Accordingly, conventionally breathing assistance devices were controlled in a manual fashion by a medical practitioner who set and then adjusted the operational parameters of the breathing assistance device every so often. This was detrimental since if the user started experiencing respiratory distress it was not conventionally possible to automatically adjust the breathing assistance device to reduce the respiratory distress encountered by the user which may be fatal in some situations where response time is critical for adjusting the operation of the breathing assistance device. More recently, other techniques including traditional FOT/Oscillometry have been used to automatically adjust the parameters of breathing assistance devices. However, traditional FOT uses averaging and therefore there is a delay of multiple seconds before any detection can happen. This is also detrimental to the user/patient's health and comfort. Moreover automatic adjusting of breathing assistance devices utilizing techniques such as only sensing the airflow or oxygen levels does not provide enough information of the health of the complete respiratory system.

It is believed that the technique of determining the comfort level index of a user of a breathing assistance device and generating a control signal to control the breathing assistance device to maintain the comfort level index of the user in a certain range where the user is not under distress, in accordance with the teachings herein, will increase the rate of adoption of use of breathing assistance devices where the use is voluntary (i.e. as for sleep apnea devices). This method also provides technical advantages such as an increase in the speed of adaptation of the breathing assistance device to any respiratory distress encountered by the user as the method can detect the respiratory distress relatively quickly and can also react quickly to such distress and control the breathing assistance device to reduce the level of respiratory distress that is encountered by the user. This can be critical in some cases where increased respiratory distress can have significant, if not fatal, consequences to the user.

Referring now to FIG. 1, illustrated therein is a block diagram of a breathing assistance system 100 for controlling or tuning a breathing assistance device using the forced oscillation technique in accordance with at least one embodiment of the teachings herein. The system 100 comprises a breathing assistance device 102 that generates an airflow that is provided to a user 110 via air transport pathways 104 and 108 and, for example, a laryngeal tube, a breathing mask or an endotracheal tube 109 (hereinafter collectively referred to as an "entry element"). The airflow can be at least one pressure pulse of air, a continuous flow of air, or a superposition of pressure pulses of air and a continuous flow of air. The airflow is controllable by adjusting at least one of the air pressure and flow rate via corresponding input controls on the breathing assistance device.

In some embodiments, the breathing assistance device 102 may be a mechanical ventilator for providing breathing support to the user. In other embodiments, the breathing assistance device 102 may be a CPAP or PAP device for providing breathing support to the user. In other embodiments, the breathing assistance device 102 may be a respiratory treatment delivery device such as, but not limited to, respiratory treatment delivery devices that assist a user in clearing their lungs and coughing out secretions.

A breathing assistance device controller 106 is coupled to the breathing assistance device 102 via the air transport pathway 104 (which may also be called the flow passage 104) and receives airflow from the breathing assistance device 102 and delivers the airflow via the air transport pathway 108 and the entry element 109 to the user 110. It should be noted that the term "air" in the present disclosure is used generally to denote the flow of gas and other particles through the system. For example, the output of a mechanical ventilator may include gasses and/or vapors other than air such as, but not limited to, anesthetics, for example which are typically vapors but can also be gases. In a PAP device, water vapor may be combined with air. In some embodiments of the breathing assistance device, gaseous medication (i.e. steroids, oxygen, Nitrogen, etc) may be added to the air flow and provided to the patient under ventilation based on respiratory health and/or measured comfort level. For example, the medication may include an appropriate amount of steroids that may be used daily to improve the CPAP experience for the user. The airflow may be delivered to the user 110 via the entry element 109. In the present embodiment, the entry element 109 may be a mask worn over the user's 110 nose and mouth or just over the nose for alternative masks. In other embodiments, the entry element 109 may be an endotracheal tube inserted into the trachea by means of intubation or tracheostomy.

In embodiments in which the breathing device 102 is a mechanical ventilator, there are actually two air pathways (not shown) instead of just the air transport pathway 104 (which may also be called a flow passage) where one of the pathways is used for inhalation and the other of these pathways is used for exhalation. The pathways shown in FIG. 1 apply for the case where the breathing assistance device 102 is a PAP device. It may be thus understood that the breathing assistance device 102 provides at least one pathway to allow air to flow from the air transport pathway 104 to the air transport pathway 108. It may further be understood that there can be embodiments in which the breathing assistance device controller 106 is at least partially or completely incorporated "inline" with the airflow pathways from the breathing assistance device 102 to the user 110.

In the present example embodiment, the breathing assistance device controller 106 comprises one or more sensors (not shown) to measure the various parameters of the airflow being delivered to the user 110. For example, sensors can be attached to the mask worn by the user 110 which may result in ideal SNR. Alternatively, the sensors, such as ultrasonic sensors for example, can be attached in the tubing pathway. In either case, these sensors can be used to measure both inspiration and expiration. However, in the case of a PAP machine, such sensors are located be close to the mask because the tube only carries an inspiratory flow whereas in a mechanical ventilator the sensors can be attached to the mask or endotracheal tube or they can be located anywhere along the tubes that are used for the inspiratory pathway and the expiratory pathway.

In some embodiments, the breathing assistance device controller 106 may not include these sensors but may instead read these parameters from the breathing assistance device 102 since the breathing assistance device 102 may also be equipped with sensors for measuring airflow parameters. The breathing assistance device controller 106 may further comprise a device to provide a forced oscillation signal, which has changes in air pressure. In some embodiments, a sensor for measuring both air pressure and airflow is present. In other embodiments, dedicated sensors may be used to measure the airflow or the air pressure such that more than one sensor may be used with the breathing assistance device controller 106. For example, some sensor technologies use a laser to detect movement or ultrasound can be used to detect both pressure and flow rate in one sensor (as the measured flow rate can be determined from dividing the measured pressure by a known resistance).

The measured airflow parameters such as air volume, air pressure and airflow may be used by the breathing assistance device controller 106 to generate a control signal 112 that can be used as feedback to adjust the operation of the breathing assistance device 102. In some embodiments, the control signal 112 may be used to adjust one or a few or all of the adjustable parameters of the breathing assistance device 102. For example, parameters that may be adjusted include at least one of the flow rate of the airflow, the volume of the airflow, the pressure of the airflow, the frequency of the airflow, the amplitude of the airflow and the phase of the airflow that can be generated by the breathing assistance device 102.

Figure 2:
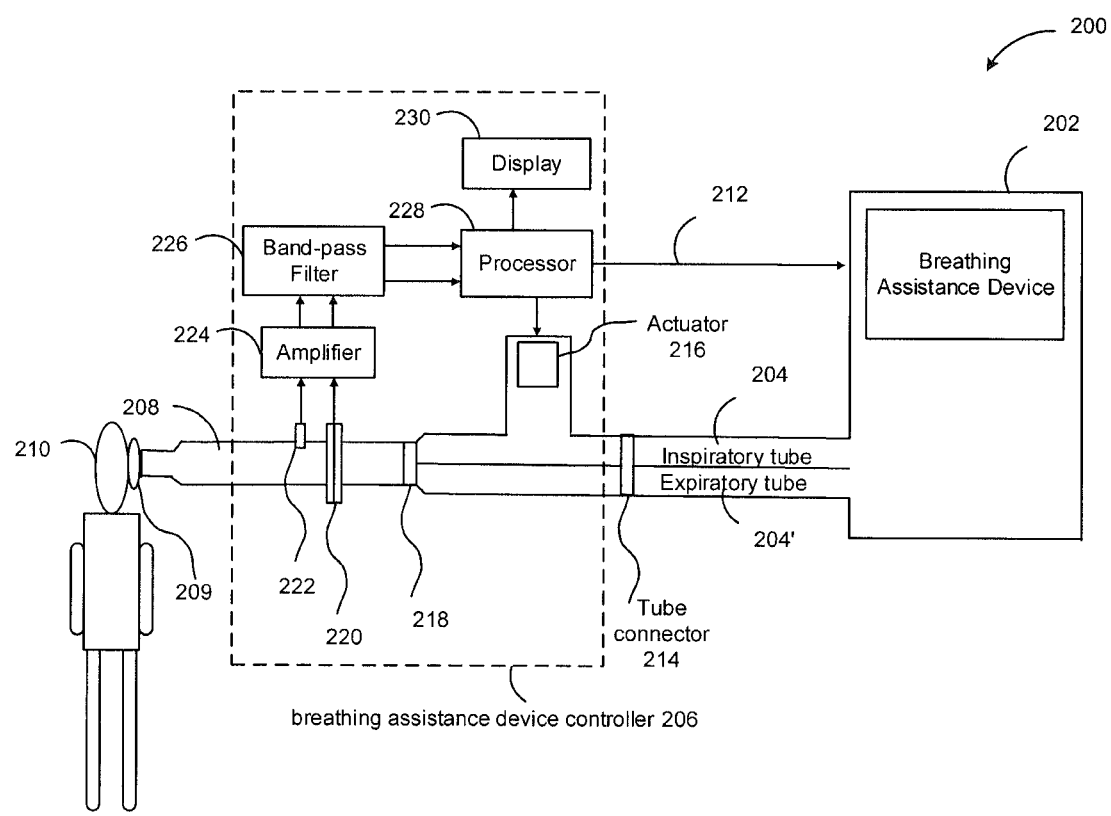
FIG. 2 is a block diagram of another example embodiment of a breathing assistance system for controlling or tuning a breathing assistance device during use by a user.

Referring now to FIG. 2, shown therein is a block diagram of an example embodiment of a breathing assistance system 200. Elements that correspond to those in FIG. 1 have been numbered similarly. Similar to the configuration of the breathing assistance system 100, a breathing assistance device 202 generates airflow that is provided to a user 210 via air transport pathways 204 and 204' and the breathing tube 208 and the airflow is monitored by a breathing assistance device controller 206 for modifying the operation of the breathing assistance device 202. Similar to FIG. 1, the airflow may be delivered to the user 210 via an entry element 209. In this example embodiment the entry element 209 may be a mask worn over the user's 210 nose and optionally the user's mouth. In other embodiments, the entry element 209 may be an endotracheal tube inserted into the trachea by means of intubation or tracheostomy.

FIG. 2 provides additional details with respect to the various system components that may be employed. In some embodiments, the breathing assistance device 202 may be a mechanical ventilator for providing breathing support. In other embodiments, the breathing assistance device 202 may be a PAP device for providing breathing support.

In the present embodiment, the breathing assistance device 202 is a mechanical ventilator and provides an inspiratory tube 204 and an expiratory tube 204' for airflow leaving and returning the breathing assistance device 202. The inspiratory tube 204 and the expiratory tube 204' may be connected to the breathing assistance device controller 206 at one airflow pathway using the tube connector 214. The airflow may then flow to the user 210 through another airflow pathway of the breathing assistance device controller 206. The airflow from the inspiratory tube 204 may be subjected to perturbation from a forced oscillation produced by a motor or an actuator (hereinafter referred to as the "actuator" to refer to both cases) 216 generating an oscillation of air at a desired frequency. The actuator may be one of a loud speaker, an electromagnet, a piezoelectric device, a piston and a motor, for example. The choice of actuator may be dependent on the design specifications such as the physical size of the device as well as on the limitations imposed on the Bill of Materials (BOM). It should be noted that in some embodiments, the actuator can be included in the breathing assistance device 202 and not in the breathing assistance device controller 206. Alternatively, in some embodiments, both the breathing assistance device 202 and the breathing assistance device controller 206 can include an actuator.

The oscillation pressure signal has an oscillation frequency that may be at any frequency that is practical for performing air pressure and airflow measurements. For example, the frequency may include, but is not limited to the range of 0.001 Hz to 100 MHz. In some embodiments, a multi-frequency signal can be used having different harmonics. For example, the oscillation signal may be a square wave or a triangular wave. Furthermore, a multi-frequency signal can be used to calculate impedance at different frequencies. The oscillation pressure signal is superimposed into the modified and/or spontaneous breathing of the user 210.

In some embodiments, the generated oscillation pressure signal may also be controlled to deliver a desired pressure. In some cases, it may be preferable to produce pressures (i.e. amplitude of the generated oscillation signal) that do not exceed a peak-to-peak value of 2 $cmH_2O$. In some other cases, the pressure may be chosen on the basis of the frequency of oscillation or on the sensitivity and precision of the flow rate/pressure sensors. In some cases, the amplitude of the oscillation (i.e. the pressure) may follow an inverse frequency trend (1/f). For example, if frequencies of 6, 11 and 19 Hz are used, the amplitude of pressure at 6 Hz is higher than the amplitude of pressure at 11 Hz. Similarly, the amplitude of pressure at 11 Hz is higher than the amplitude of pressure at 19 Hz.

The inspiratory tube 204 and the expiratory tube 204' may be combined prior to reaching the user 210 at a junction using a tube fitting 218 connected to a breathing tube 208. Subsequent to the tube fitting 218, the combined airflow may be sensed to determine parameters such as the airflow and the air pressure. In this example embodiment, a sensing system is used that comprises a flow transducer 220 and a pressure transducer 222. It should be noted that the flow transducer 220 may also be called a flow rate transducer or an airflow transducer. The sensor type used for the transducers 220 and 222 can be any appropriate transducer device, including but not limited to, ultrasonic, pneumatic and piezoelectric transducers, for example. In some embodiments, the airflow can be measured and calculated by recording the pressure drop across a pneumotachograph, which is used as the sensor.

The outputs of the flow transducer 220 and the pressure transducer 222 may be preconditioned prior to being further processed. For example, the output signals from the transducers 220 and 222 may be amplified by an appropriate amplifier 224 to obtain the desired signal amplitudes. For example, in some embodiments, the amplifier 224 may be a lock-in amplifier which may be used to reduce signal noise to help focus on the frequency of interest. It should be noted that separate amplifiers can be used for each measured signal or a dual channel amplifier may be used.

The amplified signal may then be filtered to remove extraneous frequency domain information. In the present embodiment, a band-pass filter 226 with a tuned center-frequency corresponding to the frequency of the oscillation produced by the actuator 216 may be used. In some embodiments, the passband may be made sufficiently narrow such that a notch filter can be used since a single frequency is used. The bandpass filter has a narrow passband but it is preferably large enough to contain any side lobes in the measured signals that contains modulated breathing information.

After the signals have been amplified and filtered, the signals may be received by the processor 228 for further processing and analysis in order to generate a control signal 212 that is provided to the breathing assistance device 202 to adjust its operation, as described in more detail below. In some embodiments, the processor 228 may a programmable device such as a programmable microcontroller or a field programmable gate array (FPGA). In other embodiments, the processor may be part of a single-board computer system platform such as the Arduino platform, or Raspberry Pi platform. In yet other embodiments, the signal filtering may be performed using the processor 228 such as by using digital signal processing (DSP) techniques such that separate filtering device 226 may not be necessary.

The control signal 212 can be provided to the breathing assistance device 202 using any method known to those skilled in the art. For example, the control signal 212 can be provided through a wired connection. However, in other implementations, the control signal may be communicated wirelessly to the breathing assistance device 202. The measured airflow parameters and control signal may also be shown on an optional display 230 provided on the breathing assistance device controller 206.

The breathing assistance device controller 206 can be configured to operate continuously to monitor the pressure and flowrate of the airflow provided to the user 210 to allow for constant adjustment of the operation of the breathing assistance device 202. Doing so may permit real-time or near real-time adaptive adjustments to be made to minimize any distress experienced by the user 210. In other embodiments, the breathing assistance device controller 206 may alternatively be controlled to operate intermittently, for example, at a set time interval such as every 30 seconds or every 60 seconds. Such operating conditions may be preferred if the breathing assistance device controller 206 is battery operated so as to help extend the operational lifetime of the breathing assistance device 202.

Figure 3:
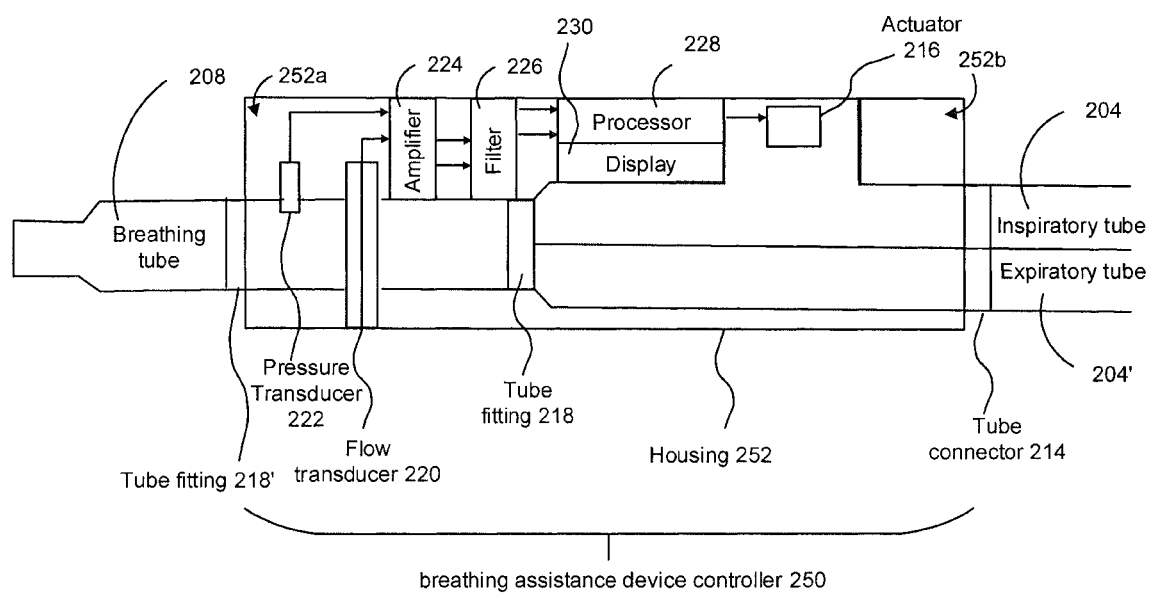
FIG. 3 is a block diagram of an example embodiment of a breathing assistance device controller that can be used with the breathing assistance system.

FIG. 3 shows an example embodiment of an integrated breathing assistance device controller 250 in which the various components needed for monitoring airflow and controlling the breathing assistance device 202 are fitted within a single device so as to allow the device to be used "inline". Hence the breathing assistance device controller 250 can be referred to as an inline device. The references numerals shown in FIG. 3 generally correspond to those described previously for the components shown in FIG. 2.

The breathing assistance device controller 250 has a housing 252 with first and second ends 252a and 252b. The end 252b can be fitted to the inspiratory tube 204 and the expiratory tube 204' via a tube connector 214. The end 252a may be attached to the breathing tube 208 using a tube fitting 218' to provide ventilation to the user 210 (not shown). It should be noted that the junction that joins the inspiratory tube 204 and the expiratory tube 204' is internal to the device 250, and the tube fitting 218 is also internal to the device 250. Therefore, in some embodiments, the breathing assistance device controller 206 can be regarded as an enhanced tube adaptor to fit, connect or join breathing tube 208 to the inspiratory tube 204 and the expiratory tube 204'.

Figure 4:
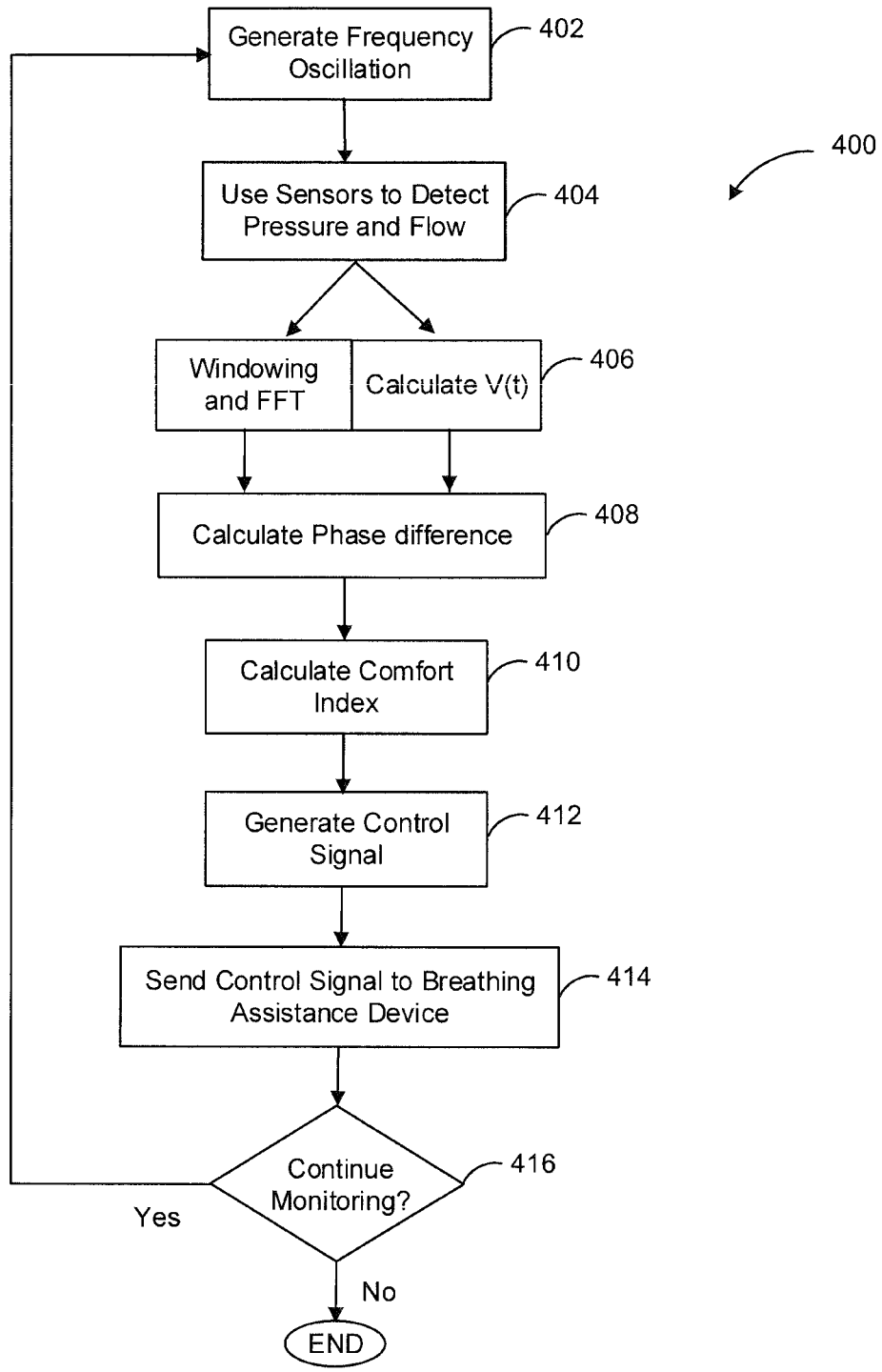
FIG. 4 is a flowchart of an example embodiment of a breathing assistance control method.

Referring now to FIG. 4, shown therein is a flowchart depicting an example embodiment of a breathing assistance control method 400 that can be used to acquire pressure and airflow information and use the information to control the operation of a breathing assistance device. For ease of explanation, the elements depicted in the breathing assistance system 200 and the waveforms in FIG. 5 shall be used to describe the various steps of the method 400. However, it should be understood that this technique can be used on the integrated breathing assistance device controller 250.

The method 400 may begin when the breathing assistance device 202 has been activated, thereby, supplying an airflow to the user 210. Starting at act 402, the processor 228 may operate the actuator 216 to generate an oscillation pressure signal having one or more oscillation frequencies within a desired frequency range. For example, in some embodiments the desired frequency range can be any frequency between 0.01 Hz-1 KHz. As mentioned previously, the oscillation may be a single frequency oscillation. However, in other embodiments, the oscillation pressure signal may comprise a number of oscillation frequencies (i.e. where the oscillation is not sinusoidal). Act 402 can be done on a continuous or periodic basis as explained previously.

At act 404, sensors in the breathing assistance device controller 206 such as the flow transducer 220 and pressure transducer 222 measure the flow rate and pressure, respectively, of the airflow (including the perturbation) that is sent to the user. The detected signal may be amplified by the amplifier 224 and filtered by, in this case, band-pass filter 226 with a center-frequency corresponding the frequency of the oscillation produced by the actuator 216. Also noted previously, in some embodiments, the passband may be made sufficiently narrow such that a notch filter can be used instead since a single frequency is used.

After the signals have been processed by applying amplification and filtering, the processed signals are received by the processor 228 for further processing. At act 406 the processor 228 may use the measured signals to determine the volume V(t) of the airflow and the mechanical impedance of the user's respiratory system over time. The volume V(t) may be determined as the integral of the flow rate signal that is measured plus a known bias or constant volume. To determine, the mechanical impedance, the processor 228 can apply a windowing function to the processed flow rate and pressure signals to help enforce periodicity and subsequently perform the Fourier transform (e.g. via fast Fourier Transform FFT) of these signals in each window. In some embodiments, the signal can be windowed for short periods, such as ⅙ seconds for a 6 Hz single frequency sinusoidal oscillation produced by the actuator 216. Under the uncertainty principle, a shorter period may lead to a loss of frequency resolution with a gain of time resolution. Generally a useful windowing period can correspond to an inverse of the maximum oscillation frequency used in the oscillation pressure signal to provide a short window that does not result in a loss of too much frequency resolution. In other embodiments, the window may be longer, such as 4 seconds, for example. It can be understood that the signals can be assumed to be sufficiently stationary due to the bandpass filtering, and because of the short windowing duration. In some embodiments, a Hanning-type or Hamming-type window can be used to further help enforce periodicity by reducing the signal amplitude near the window edges. In other embodiments, the windows can be overlapping windows (e.g. with a maximum of 50% overlap between adjacent windows). In other embodiments, other types of windows may be appropriate for use. For example, in some cases it may be possible to use certain rectangular windows.

After the windowing function has been applied, the Fourier transform of the pressure and flow rate in each time window may be used to obtain an estimate of the average mechanical impedance $Z_{rs}$ in that time window. More specifically the mechanical impedance can be expressed as a ratio between the Fourier transforms of the pressure and flow rate in each window:

$$Z_{rs}(\omega) = \frac{P(\omega)}{Q(\omega)} \quad (1)$$

where $P(\omega)$ is the FFT of the measured pressure signal and $Q(\omega)$ is the FFT of the measured flow rate signal at the angular frequency $\omega = 2\pi f$ where f is the oscillation frequency of the actuator 216. Equation 1 can be applied to determine Impedance by using pressure and flow rate measured at the airway opening of the user 210.

The mechanical impedance $Z_{rs}$ is a complex quantity with a real part corresponding to respiratory resistance ($R_{rs}$) which can be largely due to airflow resistance of intrathoracic and extrathoracic airways, lung tissue and chest wall and an imaginary part corresponding to reactance ($X_{rs}$) which can arise from elastic properties of the lung and chest wall, and the inertia of the oscillating air. The impedance can thus be described as a sum of the real and imaginary parts as shown in equation 2.

$$Z_{rs}(\omega) = R_{rs}(\omega) + jX_{rs}(\omega) \quad (2)$$

The parameters $R_{rs}(\omega)$ and $X_{rs}(\omega)$ may be characterized by fitting various respiratory models to the measured data to identify various respiratory system characteristics. For example, a commonly used model is the Single Compartment Model in which $R_{rs}(\omega)$ may be assumed to be constant with frequency $\omega$ so that $$X_{rs}(\omega) = \omega I_{rs} - \frac{E_{rs}}{\omega},$$

where $E_{rs}$ and $I_{rs}$ can be idealized lumped elements that represent the elastance and inertance of the respiratory system, respectively. Accordingly, examples of respiratory system characteristics include reactance/elastance and also inertance.

It may be also noted that the determination of the resistance and reactance in each time window yields continuous functions with respect to time, $R_{rs}(t)$ and $X_{rs}(t)$, for the chosen frequency of oscillation. In cases where multiple frequencies are used in the FOT oscillation signal, then the resistance and reactance may be calculated in the manner described above for each frequency separately. A separate time course behavior of the $R_{rs}(t)$ and $X_{rs}(t)$ may be developed for each frequency considered for analysis. Alternatively, the mean values of $X_{rs}$ may be examined for different frequencies by plotting the mean values of $X_{rs}$ against oscillation frequency. Similarly, the same may be done for $R_{rs}$. It may be noted that there may be a single band-pass filter that may be configured to sequentially filter each frequency separately or there may be multiple band-pass filters each tuned at a unique frequency from the set of oscillation frequencies that are used contemporaneously to perform filtering (e.g. a comb filter). As noted previously the volume, $V(t)$ may be determined as the integral of the flow rate signal.

Figure 5:
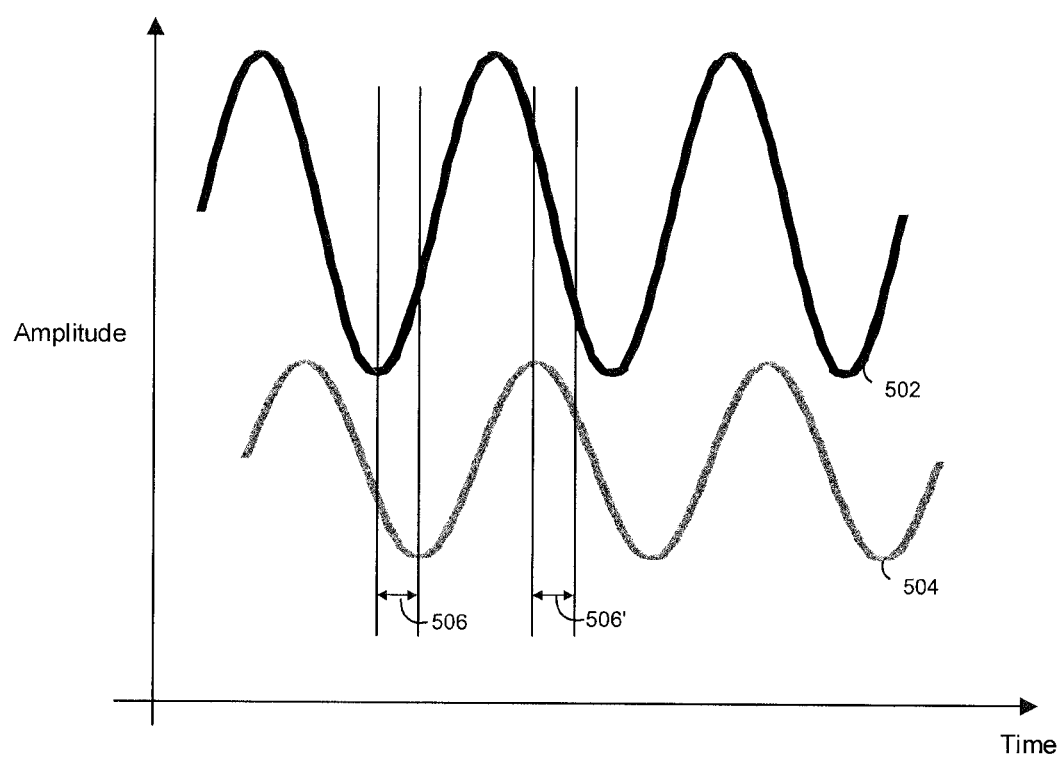
FIG. 5 shows example waveforms for a volume signal $V(t)$ and a corresponding determined reactance $X_{rs}(t)$.

FIG. 5 shows plots of amplitude versus time for example waveforms for a volume signal $V(t)$ 502 and a corresponding determined reactance signal $X_{rs}(t)$ 504. A phase difference 506 and 506' can be observed between the reactance signal 502 and the volume signal 502. This phase difference may be used to detect the severity of a user's respiratory problem or current respiratory state, which may be correlated to the percentage of open airways or non-aerated lung tissue, and compensate for it by controlling the breathing assistance device.

At act 408, the phase difference between the phase of the volume signal $\Phi_V$ and the phase of the reactance signal $\Phi_{X_{rs}}$ is determined for a particular moment in time. The phase difference can reflect the specific portion of the reactive/elastic part of the user's respiratory system that is distancing or deviating itself from the elastic part and influencing the resistive part instead. The result of this deviation can cause distress for the user since it may manifest physically as either an obstruction of their airways or a deep distress to their respiratory system due to various factors including, but not limited to, derecruitment of certain lung regions, increased heterogeneity of the user's lungs or the presence of liquid in the user's lungs. As such the determined parameters can thus be used to perform at least one of: tuning of the breathing assistance device 202 to minimize distress; diagnosis or identification of the presence of respiratory disease; and operating the breathing assistance device 202 to obtain therapeutic outcomes, for example, with respect to adjusting the operating parameters of the breathing assistance device 202 such as at least one of the pressure, flow rate, and moisture of the generated airflow to help COPD patients to breathe or expectorate.

At act 410 the phase difference can be used to determine a respiratory health status index as a function of time in accordance with equation 3.

$$H(t)=1-2\times(\Phi_V-\Phi_{X_{rs}})/\pi \qquad (3)$$

The decision of whether to adjust the operational parameters of the breathing assistance device 202 may be determined based on the values of the respiratory health status index over time. For example, if the breathing assistance device 202 is a PAP device, the extent of positive pressure applied to the respiratory system of the user 210 over time $P_{RPAP}(t)$ may be determined with the following relationship:

$$P_{RPAP}(t)=H(t)\times k_{RPAP}\times P_{CPAP} \qquad (4)$$

where $k_{RPAP}$ is an empirical coefficient for the application of reactive positive airway pressure (RPAP) which can vary in different patient/user populations, and $P_{CPAP}$ is a base/initial constant pressure that normal PAP machines can apply. A patient's comfort level index can be defined as: $Comf(t)=H(t)\times k_{RPAP}$. Accordingly, the determined reactive positive pressure $P_{RPAP}(t)$ may be used to generate a control signal at act 412 that can be applied to the breathing assistance device 202 to adjust the positive pressure $P_{CPAP}$ produced by the PAP machine. For example, if a patient's comfort level index is at a very high level for 2 seconds and then drops to half of the level for 4 seconds, the control signal can be determined to compensate for this change in the comfort level and control the PAP device to apply 0 (i.e. default air pressure) for 2 seconds and twice the default pressure for the next 4 seconds. In some embodiments, this process is updated every few hundreds of milliseconds to provide an essentially real-time response. In other embodiments, this process can be updated continuously. In some other embodiments, the frequency of update can be a predetermined frequency. This flexibility in updating the control parameters of the breathing assistance device is useful because it allows for tailoring to a particular user.

In embodiments in which the breathing assistance device 202 is a mechanical ventilator in which volume controlled modes may be selected, the air volume applied to the respiratory system of the user 210 over time $V_{MV}(t)$ can be determined with the following relationship:

$$V_{MV}(t)=H(t)\times k_{P_{MV}}\times V'_{MV} \qquad (5)$$

where $k_{P_{MV}}$ is an empirical coefficient for the application of air volume which can vary in different populations, and $V'_{MV}$ is a constant target volume provided by conventional breathing assistance devices when they are operated in a volume controlled mode. The air volume $V_{MV}(t)$ can similarly be used to generate a control signal to control the operation of the breathing assistance device when it is a mechanical ventilator operating in a volume controlled mode.

In yet other embodiments, in which the breathing assistance device 202 is a mechanical ventilator which operates in a pressure controlled mode, the air pressure applied to the respiratory system of user 210 over time $P_{MV}(t)$ can be determined with the following relationship:

$$P_{MV}(t)=H(t)\times k_{P_{MV}}\times P'_{MV} \qquad (6)$$

where $k_{P_{MV}}$ is an empirical coefficient for the application of air volume which can vary in different populations, and $P'_{MV}$ is the target pressure that conventional mechanical ventilators operating in a pressure controlled mode is set to apply. The air pressure, volume and flow rate limits, cycle, and trigger can similarly be used to generate a control signal to control operation of the breathing assistance device operating in pressure controlled mode.

At act 414 the generated control signal is sent to the breathing assistance device. At act 416, the method determines whether monitoring of the user's breathing distress level and subsequent adjustment of the breathing assistance device (if needed) should be continued. If not, the method 400 proceeds to act 416 and ends. If the method 400 is continued, then the method proceeds to act 402 where the oscillation pressure signal is generated and the acts of the method 400 are performed again.

The preceding paragraphs illustrate the advantages of the described embodiments according to the teachings herein since they are able to fill a gap in current breathing assistance devices where there is a lack of continuous information about the condition of the user's respiratory system and the resulting comfort level or harm level of the user. It may be appreciated that a further advantage of having a breathing assistance device controller that is small in size and is light weight is that it is adaptable for use with any breathing assistance devices by using different tube adapters. While the use of different adaptors may also require compensation for tubing resistance, in at least some embodiments the actuator 216 can be kept out of the main tubing path, so that it that does not add any extra resistance to the tubing (e.g. <0.6 cmH$_2$O/L/s). Also the breathing assistance device controller and/or systems that utilize the controller may be further simplified by operating at a single frequency. Although known single frequency FOT machines commonly operate at a frequency close to breathing (e.g. 4-5 Hz), the various embodiments described herein can operate at a higher frequency which allows for the use of a smaller, lighter actuator 216, that enables the breathing assistance device controller to have lower power consumption, more precise signal processing and a smaller footprint so that it can more easily be used with existing breathing assistance devices in an inline fashion. This is because higher frequencies are not contaminated as much by breathing noise which leads to higher Signal to Noise Ratio (SNR). Consequently, the required amplitude of oscillation becomes smaller and may be provided by an actuator that is smaller and lighter and perhaps cheaper. Furthermore, using a higher frequency of oscillation also reduces the discomfort that the user (e.g. patient) receives from sensing vibrations in the airflow that is provided to them.

While the applicant's teachings described herein are in conjunction with various embodiments for illustrative purposes, it is not intended that the applicant's teachings be limited to such embodiments as the embodiments described herein are intended to be examples. On the contrary, the applicant's teachings described and illustrated herein encompass various alternatives, modifications, and equivalents, without departing from the embodiments described herein, the general scope of which is defined in the appended claims.

The invention claimed is:

1. A system for providing breathing assistance to a user, wherein the system comprises:
   a breathing assistance device that generates an airflow comprising at least one pressure impulse or a continuous pressure flow rate;
   an entry element that is coupled to the breathing assistance device and is worn by the user to provide the airflow to the user during use; and
   a breathing assistance device controller that is coupled to the breathing assistance device to adjust the operation of the breathing assistance device during use via a control signal that is generated based on a comfort level index that is determined to indicate a respiratory health status for the user, the comfort level index being based on a phase difference between airflow and respiratory system parameters of the user.

2. The system of claim 1, wherein the breathing assistance device is one of a mechanical ventilator and a continuous positive airway pressure device.

3. The system of claim 1, wherein the breathing assistance device controller comprises:
   sensors for measuring air pressure and flow rate of the airflow and generating measured pressure and flow rate signals; and
   a processor that is electronically coupled to the sensors to receive the measured signals, to determine at least one respiratory system characteristic for the user based on the measured signals; to determine the comfort level index based on the measured flow rate signal and the at least one respiratory system characteristic; and to generate the control signal based on a relationship between the comfort level index and the type of breathing assistance device, the at least one respiratory system characteristic including reactance/elastance or inertance.

4. The system of claim 3, wherein the system comprises an actuator that is electrically coupled to and controlled by the processor to generate an airway pressure perturbation that is superimposed on the airflow that is provided to the user.

5. The system of claim 4, wherein the breathing assistance device comprises the actuator or the breathing assistance device controller comprises the actuator.

6. The system of claim 4, wherein the airway pressure perturbation is generated to have at least one frequency.

7. The system of claim 6, wherein the at least one frequency is in a frequency range of 0.001 Hz to 100 MHz.

8. The system of claim 3, wherein the processor is configured to determine a complex respiratory impedance and a respiratory volume for the user's respiratory system based on the at least one of the measured air pressure and flow rate signals.

9. The system of claim 8, wherein the respiratory device controller is further configured to determine a phase difference between an imaginary portion of the complex respiratory impedance and the respiratory volume.

10. The system of claim 1, wherein the respiratory device controller has a housing with a first end that is releasably coupled to the breathing assistance device via a first airflow pathway and a second end that is releasably coupled to the entry element by a second airflow pathway.

11. The system of claim 1, wherein gaseous medication comprising one or more of steroids, oxygen, and Nitrogen is added to the air flow before providing the airflow to the user based on at least one of the user's respiratory health and the comfort level index.

12. The system of claim 1, wherein the determining of the comfort level index and the generating of the control signal is performed continuously or periodically to provide a real-time response.

13. A breathing assistance device controller for controlling the operation of a breathing assistance device that provides breathing assistance to a user, wherein the controller comprises:
   sensors for measuring airflow parameters of the airflow and generating measured signals; and
   a processor that is electronically coupled to the sensors to receive the measured signals and to generate a control signal based on a comfort level index that is determined to indicate a respiratory health status for the user, the comfort level index being based on a phase difference between the measured signals and at least one characteristic of the user's respiratory system to adjust the operation of the breathing assistance device during use, the at least one respiratory system characteristic including reactance/elastance or inertance.

14. The controller of claim 13, wherein the processor is configured to:
   determine at least one respiratory system characteristic for the user based on the measured signals; and
   generate the control signal based on a relationship between the comfort level index and the type of breathing assistance device.

15. The controller of claim 13, wherein the controller further comprises:
   a first airflow pathway for receiving an airflow generated by the breathing assistance device; and a second airflow pathway for providing the airflow to an entry element used by the user.

16. The controller of claim 13, wherein the controller further comprises an actuator that is electrically coupled to and controlled by the processor to generate an airway pressure perturbation that is superimposed on the airflow that is provided to the user while the sensors perform the measurements.

17. The controller of claim 16, wherein the airway pressure perturbation is generated to have at least one frequency.

18. The controller of claim 17, wherein the at least one frequency is in a frequency range of 0.001 Hz to 100 MHz.

19. The controller of claim 14, wherein the processor is configured to determine a complex respiratory impedance and a respiratory volume for the user's respiratory system based on the measured signals.

20. The controller of claim 19, wherein the controller is further configured to determine a phase difference between an imaginary portion of the complex respiratory impedance and the respiratory volume.

21. The controller of claim 14, wherein the processor is configured to determine the comfort level index for the user at a predefined frequency that corresponds to the at least one frequency of the airway pressure perturbation signal.

22. The controller of claim 13, wherein the processor is configured to generate the control signal such that the resultant airflow generated by the breathing assistance device based on the control signal is used for the treatment of a respiratory condition thereby improving respiratory health status for the user.

23. The controller of claim 13, wherein gaseous medication comprising one or more of steroids, oxygen, and Nitrogen is added to the air flow before providing the airflow to the user based on at least one of the user's respiratory health and the comfort level index.

24. A method of for adjusting an airflow provided by a breathing assistance device to a user, wherein the method comprises:
    measuring airflow parameters of the airflow and generating measured signals;
    operating a processor that is electronically coupled to the sensors to receive the measured signals and to generate a control signal based on a comfort level index that is determined to indicate a respiratory health status for the user, the comfort level index being based on a phase difference between the measured signals and at least one characteristic of the user's respiratory system, the at least one respiratory system characteristic including reactance/elastance or inertance; and
    sending the control signal to the breathing assistance device to adjust the operation of the breathing assistance device during use.

25. The method of claim 24, wherein the act of measuring comprises measure a pressure and a flow rate of the airflow that is provided to the user and generating measured pressure and flow rate signals.

26. The method of claim 24, wherein the method further comprises
    determining at least one respiratory system characteristic for the user based on the measured signals; and
    generating the control signal based on a relationship between the comfort level index and the type of breathing assistance device.

27. The method of claim 24, wherein the method further comprises determining a phase difference between an imaginary portion of the complex respiratory impedance and the respiratory volume.

* * * * *